(12) United States Patent
Fernandez de la Mora et al.

(10) Patent No.: US 8,278,622 B2
(45) Date of Patent: *Oct. 2, 2012

(54) METHOD AND APPARATUS TO ACCURATELY DISCRIMINATE GAS PHASE IONS WITH SEVERAL FILTERING DEVICES IN TANDEM

(75) Inventors: Juan Fernandez de la Mora, New Haven, CT (US); Alejandro Casado, Boecillo (ES); Gonzalo Fernandez de la Mora, Madrid (ES)

(73) Assignee: Sociedad Europea de Analisis Diferencial de Movilidad, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 12/946,435

(22) Filed: Nov. 15, 2010

(65) Prior Publication Data

US 2011/0057096 A1 Mar. 10, 2011

Related U.S. Application Data

(63) Continuation of application No. 12/070,937, filed on Feb. 23, 2008, now Pat. No. 7,855,360.

(60) Provisional application No. 60/903,251, filed on Feb. 24, 2007.

(51) Int. Cl.
*G01N 15/00* (2006.01)
(52) U.S. Cl. ........ 250/294; 250/281; 250/282; 250/288; 250/290; 250/291; 250/292; 250/297
(58) Field of Classification Search .............. 250/281, 250/282, 288, 290, 291, 292, 297
See application file for complete search history.

(56) References Cited

U.S. PATENT DOCUMENTS

| 6,495,823 | B1 | 12/2002 | Miller et al. | |
|---|---|---|---|---|
| 6,498,342 | B1 | 12/2002 | Clemmer | |
| 6,559,441 | B2 | 5/2003 | Clemmer | |
| 6,784,424 | B1 | 8/2004 | Willoughby et al. | |
| 6,794,641 | B2 | 9/2004 | Bateman et al. | |
| 6,806,463 | B2 | 10/2004 | Miller et al. | |
| 6,815,668 | B2 | 11/2004 | Miller et al. | |
| 6,822,224 | B2 | 11/2004 | Guevremont | |
| 6,960,761 | B2 | 11/2005 | Clemmer | |
| 7,015,466 | B2 | 3/2006 | Takats et al. | |
| 7,164,122 | B2 * | 1/2007 | Fuhrer et al. | ............. 250/287 |
| 7,228,091 | B2 | 6/2007 | Hays et al. | |

(Continued)

*Primary Examiner* — David A Vanore
(74) *Attorney, Agent, or Firm* — Hoffmann & Baron, LLP

(57) ABSTRACT

A method for fast and accurate recognition of species contained in trace amounts in complex mixtures such as ambient air or biological fluids is taught based on the use in tandem of one or several differential mobility analyzers (DMAs) and possibly also a mass spectrometer (MS), all arranged in series. The two DMAs operate in different regions of the ion drag versus drift velocity curve (for instance, linear versus nonlinear regions), hence separating according to more than one independently discriminating parameters of the ion. Very high discrimination can be achieved even with a single stage of mass spectrometric separation by selecting a narrow range of ions with the DMA, and analyzing them in the MS, first without fragmentation, and then with fragmentation. This process does not require necessarily a tandem MS when fragmentation takes place in the inlet region of the MS. Fast and accurate discrimination is possible in single ion monitoring mode (SIM) for a large number of targeted species, even with relatively inexpensive and light single quadrupole MS systems, where the various filters placed in series would open pre-configured narrow windows suitable for passage of each ion in a list.

13 Claims, 1 Drawing Sheet

U.S. PATENT DOCUMENTS

| | | |
|---|---|---|
| 7,518,108 B2 | 4/2009 | Frey et al. |
| 7,521,673 B2 | 4/2009 | Arcas et al. |
| 7,851,743 B2 * | 12/2010 | Okumura ............... 250/282 |
| 7,855,360 B2 * | 12/2010 | Fernandez de la Mora et al. ............... 250/290 |
| 7,884,320 B2 * | 2/2011 | Landgraf ............... 250/288 |
| 7,888,635 B2 * | 2/2011 | Belov et al. ............... 250/283 |
| 8,063,361 B2 * | 11/2011 | Wu et al. ............... 250/288 |
| 2010/0282961 A1 * | 11/2010 | Miller et al. ............... 250/282 |
| 2011/0042559 A1 * | 2/2011 | Klepel ............... 250/282 |
| 2011/0121170 A1 * | 5/2011 | Park ............... 250/282 |
| 2011/0220790 A1 * | 9/2011 | Sun et al. ............... 250/288 |
| 2011/0266435 A1 * | 11/2011 | Hoyes et al. ............... 250/282 |
| 2011/0291001 A1 * | 12/2011 | Hoyes et al. ............... 250/283 |

\* cited by examiner

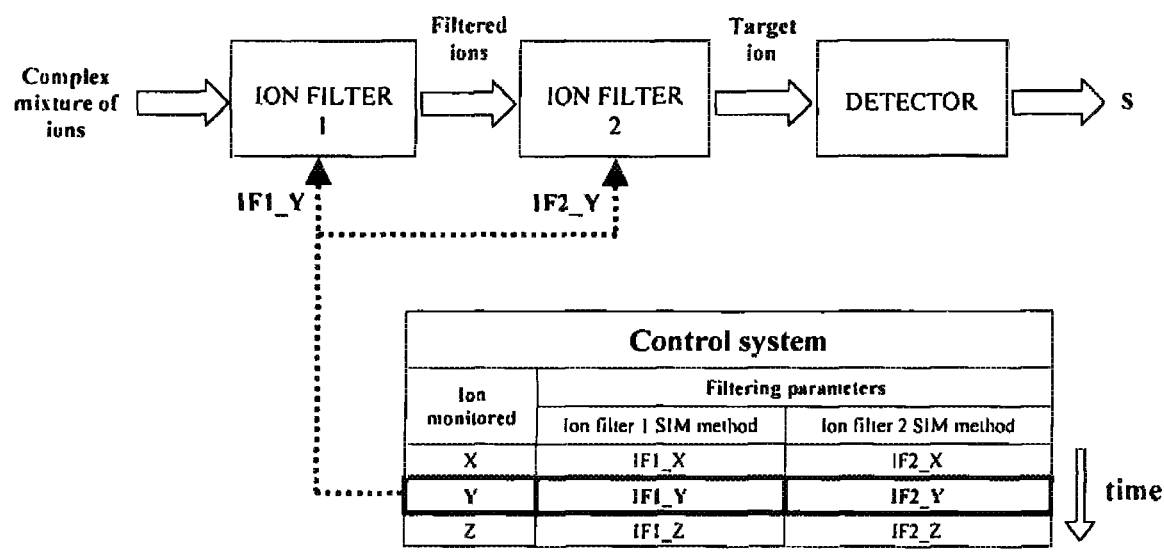

US 8,278,622 B2

METHOD AND APPARATUS TO ACCURATELY DISCRIMINATE GAS PHASE IONS WITH SEVERAL FILTERING DEVICES IN TANDEM

This application is a continuation of U.S. application Ser. No. 12/070,937, filed Feb. 23, 2008, now allowed, which claims priority from U.S. Provisional Patent Application No. 60/903,251 filed Feb. 24, 2007, the entire contents of these cases being incorporated by reference herein.

CITED PATENTS AND PATENT APPLICATIONS

U.S. Pat. No. 4,531,056, Jul. 23, 1985; Labowsky; M. J., Fenn; J. B., Yamashita; M. A. (1985) Method and apparatus for the mass spectrometric analysis of solutions, U.S. Pat. No. 5,869,831 (9 Feb. 1999) and U.S. Pat. No. 5,936,242 (10 Aug. 1999) J. Fernandez de la Mora, L., de Juan, T. Eichler and J. Rosell, Method and apparatus for separating ions in a gas for mass spectrometry U.S. Pat. No. 6,787,763, Sep. 7, 2004; J. Fernandez de la Mora M. J. Labowsky, J. Schmitt and W. Neilson, Method and apparatus to increase the resolution and widen the range of differential mobility analyzers (DMAs), Extended as European Patent Publication No. 1446820 (Application No '02782256.8) based on International Patent Application No W02003041114 (Application No. PCT/US 2002035020 entitled "Method and apparatus to increase the resolution and widen the range of differential mobility analyzers (DMAS)"

US Patent Application 20070272847 Labowsky, M. J. and Fernandez de la Mora, J., Ion mobility separation devices; International Application published under the patent cooperation treaty (PCT); PCT publication WO 2004/077016; PCT/US2004/005133; published 10 Sep. 2004

U.S. patent application Ser. No. 11/786,688, submitted Apr. 11, 2007; Rus, J., J. Fernandez de la Mora. Resolution improvement in the coupling of differential mobility analyzers with mass spectrometers or other analyzers and detectors U.S. Pat. No. 6,639,212; Oct. 28, 2003; R. Guevremont R. Purves, D. Barnett, Method for separation of isomers and different conformations of ions in gaseous phase U.S. Pat. No. 6,774,360; Aug. 10, 2004, R. Guevremont R. Purves, D. Barnett, FAIMS apparatus and method using carrier gas of mixed composition

OTHER REFERENCES CITED

Counterman, A. E., Hildebrand, A. E., Srebalus Barnes, C. A., and Clemmer, D. E. (2001), Formation of peptide aggregates during ESI: size, charge, composition and contribution to noise, J. American Soc. Mass Spectroin. 12, 1020-1035.

Eiceman, G. and Karpas, Z. (1994), *Ion Mobility Spectrometry*, CRC Press. Gamero-Castano, M. and Fernandez de la Mora (2000), A condensation nucleus counter CNC) sensitive to singly charged subnanometer particles; J. Aerosol Sci., 31, 757-772

Hewitt, G. W. (1957) The charging of small particles for electrostatic precipitation. Communications and Electronics, 31, 300-306.

Knutson, K. O. and Whitby, K. T., (1975) "Aerosol classification by electric mobility: Apparatus, theory and applications," J. Aerosol Sci., 6, 443-451.

Martinez-Lozano, P. and J. Fernandez de la Mora (2006), Resolution improvements of a nano-DMA operating transonically, Journal of Aerosol Science, 37, 500-512

Rader, D. J. and P. H. McMurry (1986), "Application of the Tandem Differential Mobility Analyzer to Studies of Droplet Growth and Evaporation," J. Aerosol Sci. 17:771-788.

Tammet, H. F. (1970) "The aspiration method for the determination of atmospheric-ion spectra," Trans, on Air ionization and Electroaerosols. Vol. II (Israel Program for Scientific Translations, Jerusalem. Original in Russian from 1967. Also available at http://ael.physic.ut.ee/tammet/AM/

GLOSSARY

CNC: condensation nucleus counter
API: Atmospheric pressure ionization
FAIMS: field asymmetric IMS
FWHM: Full peak width at half peak maximum
GC: Gas chromatography
IMS: Ion mobility spectrometry
LC: Liquid chromatography
m/z: mass/charge in amu
MS: Mass spectrometry
DMA: Differential mobility analyzer
QMS: Quadrupole MS
IQMS: Single stage QMS
3QMS: Triple stage QMS
R: resolution=1/FWHM
SIM: Single ion monitoring
TOF: Time of flight
Z: Electrical mobility

FIELD OF THE INVENTION

This invention is concerned with the accurate discrimination of ions, for chemical analysis, and in order to monitoring for the presence of minute quantities of chemical species highly diluted in very complex mixtures

BACKGROUND OF THE INVENTION AND PRIOR ART

There are many situations in which one needs to monitor for the presence of minute quantities of chemical species highly diluted in very complex mixtures. One class of examples is provided in drug development and medical diagnosis, where body fluids (blood, plasma, urine, breath, etc.) are monitored for the presence of certain key metabolites. Another example is given in civilian and military security, or in law enforcement applications, when one wishes to probe for the presence of extremely dilute volatile species in the atmosphere, where many thousands of other similar species naturally exist in comparable or much higher concentrations. In situations where one seeks to establish whether one or several target ions of specific interest are present or absent above a certain threshold, it is possible to avoid a complete analysis and search only for the desired target species in so called single ion monitoring mode (SIM). This mode is best achieved by use of analytical instruments acting as narrow band filters, which block the passage of most species, allowing through only specific ones having certain characteristics (say mass over charge, electrical mobility, etc., which we shall for convenience denote as the filtering parameters) very close to certain set values. One example of such narrow band filter is the quadrupole mass spectrometer, for which the filtering parameter is the mass over charge ratio of an ion. Another example is a differential mobility analyzer, for which the filtering parameter is the electrical mobility of an ion. The triple quadrupole mass spectrometer (3QMS) with an atmospheric pressure ionization source (API) is in fact one of the preferred instruments used in pharmaceutical applications for such monitoring (note however that the term atmospheric is part of a generic denomination and does not necessarily imply that it is restricted to operate under atmospheric pressure. Nor does the use of generic atmospheric pressure ionization mass spectrometers made in this invention restrict the invention to atmospheric conditions). It is often coupled with prior separation stages, such as liquid chromatography (LC, which separates dissolved species in the liquid phase), ion mobility spectrometry (IMS, which separates ions in the gas phase; see Eiceman and Karpas, 1994), etc. The triple quadrupole acts in a first stage as an ion filter allowing passage only of a narrow range of ions with fixed mass/charge ratio (m/z), then produces fragments of these species by impact with neutral gas molecules in a second stage, and analyzes finally the daughter products or fragment ions of such collisions in a third stage. The complex signature of the mass of a parent ion combined with the masses of its generally very specific fragmentation (daughter) ions is generally highly discriminating. Much greater specificity is added by LC, but this stage is rather slow compared with MS separation. Excellent additional fast discrimination has been achieved by adding IMS separation. However, conventional IMS separates ions in time, while a quadrupole mass spectrometer does so in space, whereby the combination IMS-MS is not ideal for use with quadrupoles, particularly in single ion monitoring mode (SIM). IMS-MS has nonetheless been developed into an effective technique (principally by D. Clemmer and colleagues; see Counterman et al., 2001) in combination with time of flight mass spectrometers (TOF-MS), and provides a very useful tool for complete two-dimensional mapping of mobility and mass distributions of complex mixtures. However, when the task at hand is to monitor for a discrete number of expected target ions, the quadrupole MS is considerably more effective. This has led to the development of ion mobility separation schemes where separation takes place in space rather than in time. For instance, so-called Field Asymmetric IMS (FAIMS) does just that. FAIMS has recently been developed from its Russian origins by Dr. Roger Guevremont (see for instance U.S. Pat. Nos. 6,639,212 and 6,774,360), and exists commercially coupled to triple quadrupole mass spectrometers. Although FAIMS has a relatively modest resolving power (R~15), it is claimed to be fairly effective in reducing chemical noise. Other even more sophisticated devices have been demonstrated, combining FAIMS, conventional IMS and MS to achieve a very high global discrimination power. However, the coupling of IMS with a quadrupole MS remains as inefficient in these triple combinations as in IMS-MS.

In spite of their many advantages, triple quadrupole instruments are generally relatively heavy (>100 kg) and expensive (<$200,000), and this has limited their use in certain applications. In particular, for the purpose of screening for explosives and other illegal substances, there is a need for relatively portable instruments, which has led to the wide use of IMS in airports and other security check points. IMS, however, is much less discriminating and sensitive than API-MS, and is therefore subject to two kinds of drawbacks. First, its limited sensitivity makes it impossible to sense low vapor pressure explosives in the gas phase, demanding instead slower concentration protocols. Second, IMS's limited resolution leads to a relatively high probability of false alarms, particularly when dealing with low vapor pressure substances for which very many other background vapors exist in comparable or larger concentrations. The difficulty is readily seen through the following example. The electrical mobilities Z in ambient air for most volatile species range between 1.5 and 2 cm$^2$/V/s. The best IMS instruments available are able to resolve species whose mobilities differ by 1%. This means that an IMS system can only distinguish 29 different peaks in this relevant mobility range ($1.01^{29}$~2/1.5). In cases where more such species are present, they cannot be resolved from each other, and cannot therefore be unambiguously identified. Even worse, since the number of sufficiently volatile chemicals of interest in applications such as medical diagnostics, security, analytical, etc., include many tens of thousands, many of them can have electrical mobilities differing from each other by less than 1%. The result is that, when monitoring for a dangerous or desired substance in an IMS system at a particular electrical mobility, the appearance of a clear signal is generally associated not to the species searched for, but to one of the many others having very close mobilities. This is the well-known problem of the false positives. Its seriousness is evident from the gravity of its consequences. For instance, airports have as a result been shut down for hours leading to vast economic losses. In combat, a false alarm may force soldiers to equip themselves with masks and other heavy and inconvenient gear, leading to a serious loss of effectiveness.

There is therefore a need for reasonably portable analytical instruments with much higher discrimination power and sensitivity than IMS. One possible solution could conceivably be based on U.S. Pat. No. 5,869,831, where a differential mobility analyzer (DMA) is combined in series with a mass spectrometer. The DMA discriminates various ions according to their electrical mobility Z, similarly as conventional IMS. However, it separates ions in space rather than in time by combining an electric field and the flow field of a gas, generally air, as described in U.S. Pat. Nos. 5,869,831 and 5,936,242, and more generally in U.S. Pat. No. 6,787,763, and in US Patent Application 20070272847. For present purposes, we will define a DMA generally as a device separating ions in space by combining an electric field and the flow field of a gas. In order to clearly distinguish DMAs from FAIMS instruments, we add the restrict on that the flow velocity in the separation region of the DMA must be comparable to the maximum instantaneous ion velocity drift caused by the electric field. More precisely, while the flow velocity can be much smaller than this maximum ionic electrical drift velocity in FAIMS devices, it is typically larger than ½ of the ion drift velocity in DMAs. DMAs can act as narrow band ion filters, taking at their ion inlet a multitude of ions with many different mobilities, and delivering at their ion outlet only those ions having a specified electrical mobility $Z_0$. This $Z_0$ is controllable through either the flow rate of gas circulating through the DMA, or the voltage difference between two or more DMA electrodes or grids. The later parameters are generally referred as the classification voltages, or the classification voltage when only one voltage is controlled. In what follows, without loss of generality, we shall for simplicity refer to just one classification voltage. The fact that both the DMA and the quadrupole mass spectrometer are narrow band ion filters, and the fact that the mobility-classified ions exiting the ion outlet of the DMA can be introduced into the sample inlet of the mass spectrometer permits the series operation of both filters in what we shall refer to as a tandem connection, or a coupling in series. The same coupling is possible between a DMA and other MS types. Because FAIMS constitutes also a band-pass ion filter, it can be similarly coupled to various MS types.

Many other embodiments of the principle of separation of ions in space by combining electric and fluid flow fields have been described in the literature, as reviewed in a book by H. Tammet (1970), and as discussed in US patent application 20070272847.

The DMA-MS arrangement does greatly increase the discrimination power of the MS without loss of its sensitivity to the particular mobility passed. However, the DMA is a scanning instrument, and this combination has to date been used in a mode where both the DMA and the MS were scanned, whereby the limited signal available is less efficiently used than in the IMS-TOF approach of Clemmer and colleagues. Scanning DMA-MS analyses are therefore time consuming, and incompatible with many of the security monitoring tasks previously alluded. Furthermore, use of the high discrimination potential offered by tandem mass spectrometers is available to the DMA-MS combination only when the DMA is attached to a relatively expensive and heavy tandem MS. In order to resolve these various problems, the present invention includes first a method to control a DMA combined with a relatively light and economical single stage quadrupole MS (IQMS), such that a large number of ions can be monitored in so called single ion monitoring (SIM) mode, at essentially the same speed as with MS alone, but with the much greater discrimination power offered by a DMA-MS combination. This first method then overcomes the prior slowness of DMA-MS operation, enhances the resolution of pure MS, and also increases the signal/noise ratio of pure MS. The invention includes also a second method to control a DMA-IQMS combination such as to obtain much higher discrimination powers, comparable to those offered by the ion fragmentation patterns available in tandem mass spectrometry. A third combination taught in this invention relies on two or more DMAs in series, which may be used with or without a mass spectrometer. In order for the two DMA separations to be different from each other, at least one of the two DMAs is operated in a regime of high drift speed, where the ion mobility depends on the intensity of the field.

Background on Nonlinear and Linear Mobility Separation

There have been several noteworthy precedents over which the third combination just mentioned builds up. The tandem DMA approach has been widely used in aerosol particle separations, particularly by McMurry and colleagues at U. Minnesota (Rader and McMurry, 1986). In this case the two DMAs separate according to exactly the same principle (linear mobility), but the particles separated undergo some change after being classified in the first DMA and before entering in the second DMA. The tandem DMA then provides an accurate measure of the change undergone by these particles. This approach has never been used with molecular ions, but it could be similarly used if the ions were subject to some controlled change, either physical (say by attachment of vapor molecules) or chemical (say by fragmentation, oxidation, etc.). The approach, however, is new, and is considered part of the present invention. In FAIMS-IMS, the FAIMS and the IMS stages analyze exactly the same ion, but do so according to different rules (nonlinear vs. linear mobility region). However, FAIMS-IMS is inferior to DMA-DMA for two reasons. First, part of the separation takes place in space and the other in time, which precluded efficient SIM analysis of target ions. Second, FAIMS has considerably smaller resolution than IMS or DMA. Alternatively, when two FAIMS devices are operated under different conditions of nonlinearity, the FAIMS-FAIMS combination separates entirely in space, but it offers far smaller resolution than DMA-DMA.

We shall now provide more detail on the method enabling nonlinear mobility separations in DMAs, which is simple in principle, but not in practice. The basis of ion mobility analysis is the fact that, in the presence of an electric field E, charged particles and ions move in a background gas (say air) at a drift velocity relative to the gas velocity that depends on their size, charge, structure, and interaction with the background, as well as on the magnitude of the field. For a given ion-gas combination at a certain pressure p and temperature T, the drag force D(u) exerted by the medium on the ion is a function of the mean velocity u with which the ion drifts through the gas. Similarly, the force F exerted by the field on the ion is proportional to its charge q: F=qE. Under sufficiently high pressure, and certainly under atmospheric or near atmospheric conditions, the equilibration between the electrical force and the drag is almost instantaneous, whereby the ion velocity is simply determined by the condition D(u)=qE. In general, u and D are vectors rather than scalars, and are not necessarily aligned, so that the relation between u and D is generally tensorial rather than scalar. This detail introduces additional degrees of freedom to perform the separation, but does not change the general line of reasoning to be described.

The ion drift velocity (or a certain component or average form of it) can be measured by a variety of means, while the field E can be precisely controlled, and the charge level can be determined by a number of well-known techniques, including mass spectrometry. Hence, one can in principle measure the function D(u), which is a highly discriminating signature of the ion. This characteristic curve has been measured in a number of instances, and can also be computed once the interaction potential between the ion and the surrounding gas is known. At sufficiently small velocities (or electric fields), D is generally linear with u through a coefficient often written $\beta=q/Z$:

$$D=\beta u \text{ (small } u\text{)}. \tag{1}$$

Z is then simply the ratio between the ion velocity and the magnitude of the field, and is generally referred to as the electrical mobility of the ion. The problem of operating in this most common linear regime is that the signature D(u) degrades from a full curve to a simple number, with the associated recognition or resolution problems already mentioned. On the other hand, separations carried out at high fields would probe the nonlinear region of the D(u) curve, and be therefore far more specific. Indeed, the full D(u) curve has (in theory) an infinite number degrees of freedom (hence an infinitely complex signature). This point is easily seen even in the limit of weak nonlinearity, where (treating D and u for the sake of simplicity as scalars rather than vectors) symmetry arguments show that $$D=\beta u+\alpha u^3+\ldots \tag{2}$$

Now, each ion is characterized by the two constants $\alpha$, $\beta$ rather than just one, and the probability that two ions have coincident values for both constants is drastically smaller than in the case where only one degree of freedom (mobility) is present. If one operates past the weakly nonlinear regime, under conditions where each ion is characterized by a full curve (a large or even infinite number of constants, associated for instance to the coefficients of its Taylor series expansion in powers of u), the probability that such complex signatures will coincide for two different ions becomes essentially zero. The situation is evidently similar to that of the vibrational or other spectra of various molecules, whose structural richness guaranties complete specificity.

In order to proceed with minimal ambiguity, we must now distinguish between two different sources of nonlinear drag. One is associated to the possibility that ions in a strong field and at sufficiently small pressures may attain large speeds during the intervals between two subsequent collisions, and be then subject to inelastic phenomena, such as excitation above ground level of electronic or other degrees of freedom, including chemical reactions. This situation is of evident interest, but is very unlikely to apply under atmospheric pressure conditions. The reason is that the average time between two collisions for an ion with the molecules of a gas at high pressure is too short to enable attaining ion energies in the electron volt range. The most likely situation of nonlinear D(u) behavior under relatively high pressures, and certainly under atmospheric conditions, corresponds to cases when the average ion drift speed becomes comparable to the thermal speed of the background gas. It is well known to those familiar with the kinetic theory of gases that the linear behavior (1) arises to first order upon expanding the Maxwellian velocity distribution function of the gas molecules with respect to the center of mass system of the two colliders in powers of the mean drift velocity of the ion with respect to this reference. Because of the structure of this Maxwellian function, the expansion is really in terms of the drift velocity divided by the thermal speed of the gas molecules. This thermal speed is of the order of the sound speed of the gas, with a characteristic value c=340 m/s in the case of air at room temperature. Consequently, the ion drag will be approximately linear provided that u<<c, when only the first term in the u/c expansion counts. But it will be highly nonlinear when u~c. One further objective of this invention is therefore to recognize target ions with high discrimination by attaining drift speeds exceeding c/3, ideally exceeding 2c/3, where D(u) curves in air are highly nonlinear. The invention includes of course similar measurements in other gases, and at temperatures other than ambient temperature, in which case c would be the corresponding sound velocity at the operating temperature.

In this context, one must re-examine prior art based on FAIMS, This method does not measure D(u), nor its linear asymptote (1), but it does rely on the existence of nonlinearities in the D(u) expression to separate ions at modest resolution prior to mass spectrometric analysis. Consequently it produces fields intense enough for such nonlinear effects to arise, at least mildly. In addition to its modest resolution, FAIMS relies on time varying fields, and therefore requires a very high power high-voltage power supply that makes it bulky and expensive.

Although IMS generally proceeds in the linear drag regime, it can in principle be forced into the nonlinear regime. The reason is that, as we shall later argue, electrical discharges in room temperature air can be avoided at fields sufficiently intense to drive high mobility ions at speeds of several hundreds of m/s. However, to do so is generally unpractical in IMS systems due, among other reasons, to time resolution constraints. This point is illustrated by noting that, at 300 m/s, an ion would advance 1 m in 3.3 ms. For a resolution of 100, one would then need to measure arrival times within 33 µs, which is considerably faster than IMS systems typically do. It is certainly possible to do so, but at the cost of substantial loss in amplification of the collected electrical signal, hence decreased sensitivity and increased noise. The situation would evidently be worse with a more portable system whose drift tube might be 10-20 cm rather than 1 m long. The alternative to the signal loss just noted is to use an unusually long drift tube (~10 m), but this is generally inconvenient and certainly incompatible with portability. Hence, although the notion of using D(u) signatures for accurate species recognition in IMS systems is new and is included as part of the present invention, a preferred embodiment is based on a DMA.

The DMA is a well known instrument conventionally used for mobility separation of relatively large particles (Hewitt, 1957; Knutson and Whitby, 1975). More recent embodiments capable of separating ions with high resolution have been described in U.S. Pat. Nos. 5,869,831, 5,936,242, and 6,787,763. As a result of improvements described in these documents, and other improvements reported by P. Martinez-Lozano and J. Fernandez de la Mora (2006), DMAs are presently able to attain resolving powers (the inverse of the full peak width at half maximumt, FWHH: R=1/FWHH) approaching 100. As also shown by Martinez-Lozano and Fernandez de la Mora, use of improvements taught in U.S. Pat. No. 6,787,763 make it possible to operate DMAs at sonic speed in air, without use of unduly large vacuum pumps. Note further that the ratio of ion drift speed to gas speed in the DMA gas is determined by geometrical constraints, and is approximately equal to the ratio $\Delta$/L between the gap $\Delta$ between the electrodes and the axial separation distance L of the DMA. This ratio has been close to ½ in the high speed DMAs so far tested, but may with comparable ease be made equal to 1. In such a situation ions drifting highly nonlinearly at speeds of 300 m/s could be readily analyzed.

In fact, by reducing the ratio $\Delta$/L below 1, there would be no limit to the ion speed achievable, other than the condition at which the instrument would begin to spark. For an ion with Z=2 $cm^2$/V/s, a gap of 0.5 cm and a voltage difference of 10 kV one obtains a drift velocity of 400 m/s. This field is attainable, assuring speeds well into the fully nonlinear regime for ions with mobilities above 1 or 1.5 $cm^2$/V/s.

The present invention is evidently not restricted to any specific DMA geometry, but applies generally to situations where ions are separated in space by traveling through a medium where a flow field and an electric field are created, whatever the geometry and the means to do so. It also applies to IMS instruments relying on ion separation in time.

DESCRIPTION OF THE DRAWING

The drawing depicts schematically the arrangement of components in the invention, with at least two narrow band ion filters placed in series, with controls enabling sequentially in time the passage of certain target ions through all filters, according to a pre-programmed schedule. A detector measures the signal S of target ions passed, and some control logic (not shown) launches an alarm or a different measurement method.

DESCRIPTION OF THE INVENTION

A first embodiment of the invention couples a DMA in series with a single quadrupole mass spectrometer (IQMS), for instance, by any of the methods proposed in U.S. patent application Ser. No. 11/786,688 by Rus and Fernandez de la Mora. The approach is illustrated in the drawing for the case where the first ion filter is a DMA and the second ion filter is a single quadrupole mass spectrometer. In this case, the mass spectrometer also contains the detector, which provides an output signal S that may be used by the Control system (shown at the bottom of the drawing) to launch an alarm signal, or to launch a different measurement sequence. The IQMS is controlled as in conventional SIM, where a list of target ions to be monitored (schematically named X, Y, Z in the drawing) is assigned by the operator, each with its given m/z, polarity (positive or negative) as well as other parameters such as desired focusing voltages, dwell time over which the MS detector will collect signal for each particular ion, etc. The various filtering parameters associated with target ion X in the second ion filter are schematically referred in the drawing as IF2_X.

The DMA is controlled also in SIM mode, where, for each target ion to be monitored, an appropriate setting of the DMA is assigned, fixing the sheath gas flow rate, classification voltage, and other filtering parameters available such that each such set of parameters most favors transmission through the DMA of the selected ion from the list. The various filtering parameters associated with target ion X in this first ion filter are schematically referred in the drawing as IF1_X. The control system varies the control parameters sequentially in time (downward time arrow at bottom right of the FIGURE), first such as to pass target ion X, then target ion Y, then target ion Z, etc. Because a suitably designed DMA can shift from one ion to another within less than 1 ms, the DMA and the IQMS are controlled approximately in synchrony, so that the settings of both allow the passage of the same ions during the dwell time of each of them. This control is schematically shown in the drawing (for the case where target ion Y is monitored) by means of arrows with broken lines connecting the control system to the ion filters. Although not shown in the drawing, the Control system may include the necessary information and logic to process the results and make decisions in real time. In this double filtration process, only the ions having simultaneously the mobility and the m/z of the target ion can pass and be counted, and those ones pass with relatively high transmission efficiencies. The method is therefore far more effective than pure MS in eliminating background noise, thanks to the removal in the DMA of contamination from many other mass peaks having very similar masses as the target ion, but slightly different mobilities. The resolving power and the sensitivity are therefore both enhanced with respect to pure MS, yet, the analysis time is not increased with respect to that of pure MS, and the total ion signal is not decreased, or is decreased only slightly.

A second method to further expand the discrimination power of the DMA-IQMS combination just discussed in the first embodiment is akin to tandem MS, and operates as follows. Once an ion is detected whose mass and mobility are within the same narrow range as a target ion, the DMA is set to pass that ion, while the lenses in the entrance region of the MS change into a fragmentation mode. The fragmentation device is not shown in the FIGURE, as it is often part of an API-MS. However, the invention includes other less conventional fragmentation schemes taking place upstream of the MS. Various schemes exist to fragment ions at the inlet of single quadrupoles, where the ingested gas moves propelled only by pressure differences, while the ions may be accelerated to considerably higher velocities by electric fields. This takes place at pressures considerably lower than atmospheric, leading to collisions between the ions and the neutrals at sufficient energies to cause fragmentation of the ions. This process is generally not as well controlled as its analog taking place in the second quadrupole cell of a triple quadrupole MS. It is generally not very useful in a single quadrupole (unless it is preceded by a liquid chromatography), since all the many ions ingested would be fragmented, and the many resulting mass peaks are very hard to interpret unambiguously. However, when a DMA is placed upstream of the single quadrupole, almost all ions are removed by the DMA, with the exception of the suspected target ion, and perhaps a small number of other ions having very similar electrical mobilities. The number of such other ions can be rapidly assessed by making a first mass scan in the MS for the mobility-selected ions. If no other masses besides the target mass are detected in substantial quantities, the lens voltages required to induce fragmentation are established, and the IQMS is now run in SIM to probe for the presence of the fragment ions expected for the target ion under such fragmentation conditions. The identification of such daughter products would greatly increase the confidence of positive assignment of the suspected target species detected as a target ion in the list. The absence of these daughter products would do the opposite.

In situations where greater reductions of analyzer weight and cost are at a premium with respect to the desire for a high resolving power, this invention includes a third method to increase the specificity and sensitivity of IMS based on the combination of two DMAs in tandem, with one of them at least operating at high electric fields in the nonlinear mobility regime. A preferred embodiment is represented in the drawing by ion filter 1 being a DMA operating in the linear or near linear drag regime, and ion filter 2 being another DMA operating in the nonlinear drag regime. The two DMAs operate in SIM, both at fixed gas flow rate. A steady stream of sample ions is ingested in the first DMA, is classified in it, and passes through the second DMA, after which it is sent to a detector, or possibly to another analyzer. Initially a list of target ions is established, each target ion with its associated classification voltage for each of the two DMAs, and its dwell time. The precise values of this pair of voltages is selected through previous tests to assure that each of the target ions is passed with maximum transmission through both DMAs when they are set to these two voltages. The two DMAs then go in time synchronously through the series of target ions, adjusting their voltages simultaneously and keeping them fixed through the dwell time for each of the target ions in the list. This process will typically take several seconds for a list of about one hundred target ions. For each of the ions monitored an output signal is measured in a detector. In one embodiment this detector is an electrometer receiving the charge of ions carried through the ion exit line of the second DMA. In another far more sensitive embodiment the detector is a condensation nucleus counter (CNC) capable of detecting single ions by passing them through a region containing a supersaturated gas, whereby they grow into visible sizes and are individually counted (Gainero and Fernandez de la Mora, 2000). If any of the ions in the list is sensed with a signal above a pre-established threshold, this marks a warning sign that this particular ion has been detected. In another embodiment of the invention, this initial warning is considered provisional, and a more detailed verification protocol is launched before striking an alarm signal. A preferred verification protocol keeps fixed the settings of the first DMA, such that the suspected target ion passes into the entrance of the second DMA. The second DMA is then run at one or more different velocity settings, each with the corresponding classification voltage appropriate to pass the target ion. If the suspected ion passes with comparable concentration at all these different settings, its nonlinear mobility response would be providing a very good match to that of the target ion, the provisional positive identification would be confirmed, and the alarm sounded. Otherwise the initial alarm would be declared false and ignored. In cases where the matching is good but not as good as expected, yet close enough, other more stringent but slower verification protocols can be launched. In one of them the second DMA would be scanned at several set speeds over a narrow range of voltages close to the classification voltage for the target ion at that particular speed. This would result in a peak shape for each DMA velocity, from which a curve of the voltage at the peak maximum can be obtained for each DMA speed and compared to that expected for the target ion.

In all the embodiments of the invention described, a source of ions appropriate for the desired analysis needs to be implemented. In one application, one wishes to monitor for the presence of certain volatile species in the ambient gas. In this case the device includes a suitable vapor charger upstream of the ion inlet of the first analyzer. A similar charger would be employed in another application where the target species to be analyzed are certain human metabolites present in the breath of a subject, whose metabolism one wishes to follow to diagnose any possible health problem, or to determine the effect over time of a certain medicine recently ingested. In another situation the target substances to be monitored are dissolved in a liquid, in which case their corresponding gas phase ions are produced by electrospraying (as described in U.S. Pat. No. 4,531,056) the liquid in the vicinity of the ion entry line to the DMA.

What is claimed is:

1. A method to establish the presence of one or several target ions within a mixture of ions, including the following steps:
   a) placing in series at least two narrow band ion filters, each allowing passage only of ions having narrowly defined values of a characteristic filtering parameter, where at least one of said ion filters is a differential mobility analyzer, where the filtering parameters associated to at least one of said differential mobility analyzers are set such as to pass one of said target ions,
   b) setting all said characteristic filtering parameters such that said at least two ion filters will pass one among said target ions,
   c) placing a detector following the last of said ion filters to measure an output signal associated to ions passing through all said filters,
   d) passing said mixture of ions through said at least two filters and read said output signal of said detector,
   e) modifying said target ions after passage through a first of said ion filters, said modifying being conducted by attachment of vapor molecules or by fragmentation or by chemical reaction,
   f) providing a signal based on said output signal of said detector.

2. An apparatus to analyze ions with high resolution, including two differential mobility analyzer filters placed in series, where the ions are modified after passing through the first of said two differential mobility analyzers.

3. An apparatus according to claim 2 including a detector placed downstream of the second differential mobility analyzer.

4. An apparatus according to claim 3 where said detector is either a condensation nucleus counter or mass spectrometer.

5. An apparatus according to claim 3 where said detector is a time of flight mass spectrometer.

6. A method to establish the presence of one or several target ions within a mixture of ions, including the following steps:
   a) placing in series at least two narrow band ion filters, each allowing passage only of ions having narrowly defined values of a characteristic filtering parameter,
   b) setting all said characteristic filtering parameters such that said at least two ion filters will pass one among said target ions,
   c) placing a detector following the last of said ion filters to measure an output signal associated to ions passing through all said filters where said detector is a time of flight mass spectrometer,
   d) passing said mixture of ions through said at least two filters and read said output signal of said detector,
   e) providing a signal based on said output signal of said detector,
   f) where at least one of said at least two ion filters is a differential mobility analyzer.

7. A method according to claim 6 where said mixture of ions is produced by ionizing volatile species by bringing said volatile species into contact with an ionization source.

8. A method according to claim 7 where said ionization includes an electrospray cloud.

9. A method according to claim 7 where said ionization source includes ionizing radiation.

10. A method according to claim 6, where
    a) said characteristic filtering parameters for said differential mobility analyzer are set to pass one of said target ions,
    b) some of said target ions are modified in one or several ways after passing through said differential mobility analyzer,
    c) said characteristic filtering parameters for said second ion filter are set to pass at least one of said modified target ions.

11. A method according to claim 10 where said target ions are modified by causing them to fragment.

12. A method according to claim 11 where said second ion filter is a single quadrupole mass spectrometer with an atmospheric pressure ion source.

13. A method according to claim 6 where two of said at least two narrow band ion filters are differential mobility analyzers.

* * * * *